(12) United States Patent
Khaira

(10) Patent No.: US 8,525,670 B1
(45) Date of Patent: Sep. 3, 2013

(54) TRACKING DEVICE FOR HOSPITALS, NURSING HOMES, AND PRIVATE USE

(71) Applicant: Ravinder Khaira, Carmichael, CA (US)

(72) Inventor: Ravinder Khaira, Carmichael, CA (US)

( * ) Notice: Subject to any disclaimer, the term of this patent is extended or adjusted under 35 U.S.C. 154(b) by 0 days.

(21) Appl. No.: 13/767,160

(22) Filed: Feb. 14, 2013

Related U.S. Application Data

(63) Continuation-in-part of application No. 12/888,867, filed on Sep. 23, 2010, now Pat. No. 8,400,295.

(51) Int. Cl.
*G08B 1/08* (2006.01)

(52) U.S. Cl.
USPC ............ 340/539.13; 340/539.11; 340/539.12; 340/572.1; 340/572.8; 340/572.9

(58) Field of Classification Search
USPC ............... 340/539.13, 539.12, 539.11, 572.1, 340/10.1, 572.8, 572.9
See application file for complete search history.

(56) References Cited

U.S. PATENT DOCUMENTS

| | | | |
|---|---|---|---|
| 6,169,494 B1 | 1/2001 | Lopes | |
| 6,176,425 B1 | 1/2001 | Harrison et al. | |
| 6,278,370 B1 * | 8/2001 | Underwood | ............... 340/573.1 |
| 6,396,403 B1 | 5/2002 | Haner | |
| 6,563,417 B1 | 5/2003 | Shaw | |
| D547,227 S | 7/2007 | Del Valle | |
| 7,545,274 B2 | 6/2009 | Coop | |
| 2004/0080420 A1 * | 4/2004 | Roberts | ..................... 340/573.4 |
| 2007/0241908 A1 | 10/2007 | Coop | |

* cited by examiner

*Primary Examiner* — Travis Hunnings

(57) ABSTRACT

A tracking system including a tracking device and external transceivers for tracking a patient and providing patient data is presented. The device features a base ring for securing around a patient's wrist or ankle. The base ring is locked via a tamper-detecting optical lock with an alarm component. A microprocessor with a memory component is disposed in the base ring. A universal serial bus port for transferring data to and from the memory component is operatively connected to the microprocessor. An active radio frequency identification (RFID) circuit with a unique signature is disposed in the base ring and adapted to autonomously transmit signals to a first external transceiver. When the RFID communication is lost, the device automatically starts a secondary transceiver disposed within the device to transmit signals to a second external transceiver. The signals include the unique signature and the location of the tracking device.

20 Claims, 5 Drawing Sheets

TRACKING DEVICE FOR HOSPITALS, NURSING HOMES, AND PRIVATE USE

CROSS REFERENCE

This application claims priority to U.S. patent application Ser. No. 12/888,867, filed Sep. 23, 2010, the specification(s) of which is/are incorporated herein in their entirety by reference.

FIELD OF THE INVENTION

The present invention is directed to tracking systems, more particularly to a novel tracking device for managing patients in hospitals, nursing homes, or for private use.

BACKGROUND OF THE INVENTION

Patient tracking in hospitals is extremely difficult. Most hospitals use paper systems (e.g., charts, dry erase boards) or computer systems to manage patients, but patient tracking cannot be done in real-time. The present invention features a novel tracking device for tracking patients in a hospital. The tracking device of the present invention can help improve patient management and even help improve infant recovery if a kidnapping occurs. The tracking device of the present invention features an optical lock and a para-aramid synthetic fiber (e.g., Kevlar®) housing with a reinforced casing, making the device difficult to remove or break.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

A tracking system including a tracking device and external transceivers for tracking a patient and providing patient data is presented. The device features a base ring for securing around a patient's wrist or ankle. The base ring is locked via a tamper-detecting optical lock with an alarm component. A microprocessor with a memory component is disposed in the base ring. A universal serial bus port for transferring data to and from the memory component is operatively connected to the microprocessor. An active radio frequency identification (RFID) circuit with a unique signature is disposed in the base ring and adapted to autonomously transmit signals to a first external transceiver. When the RFID communication is lost, the device automatically starts a secondary transceiver disposed within the device to transmit signals to a second external transceiver. The signals include the unique signature and the location of the tracking device.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
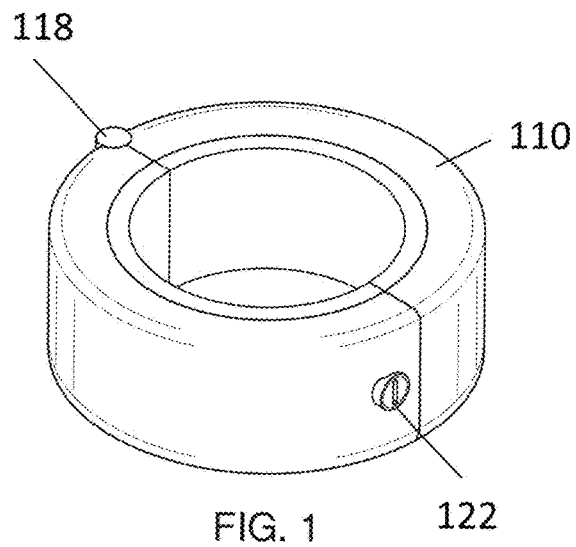
FIG. 1 is a front perspective view of the tracking device of the present invention.
Figure 2:
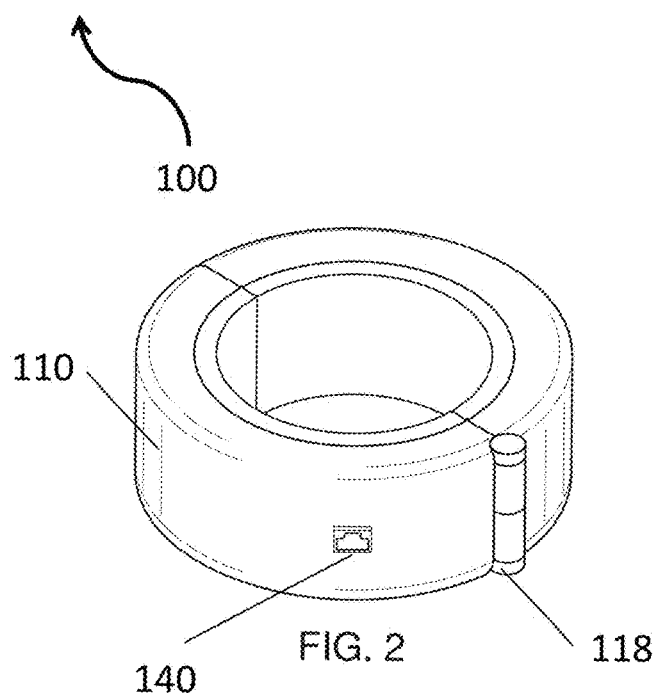
FIG. 2 is a back perspective view of the tracking device of the present invention.
Figure 3:
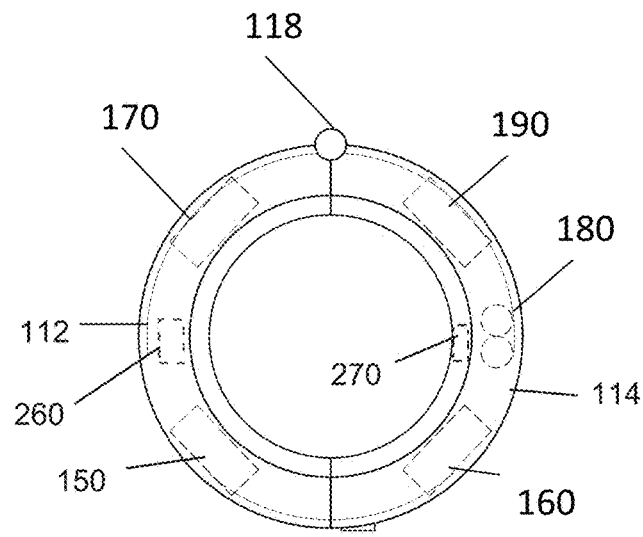
FIG. 3 is a first top view of the tracking device of FIG. 1, wherein the device is in the closed position.
Figure 4:
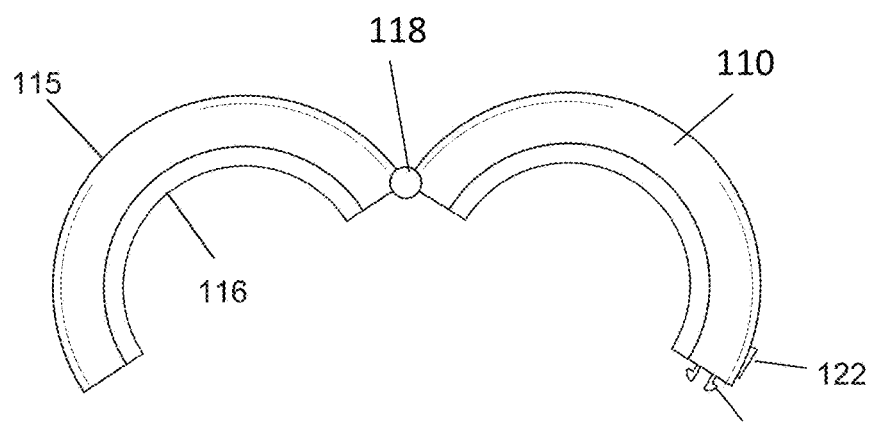
FIG. 4 is a second top view of the tracking device of FIG. 1, wherein the device is in the open position.
Figure 5:
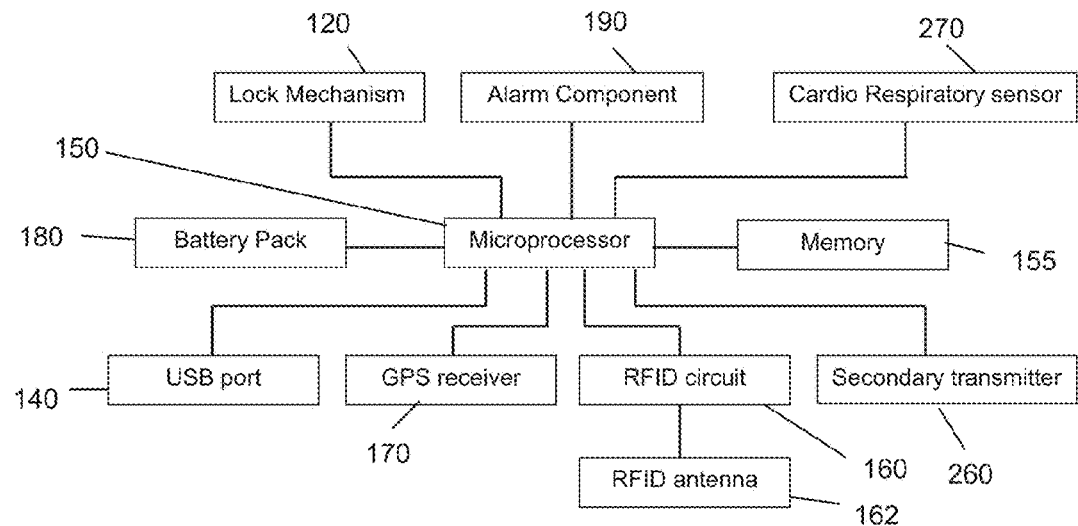
FIG. 5 is a schematic representation of the electrical components of the tracking device of the present invention.
Figure 6:
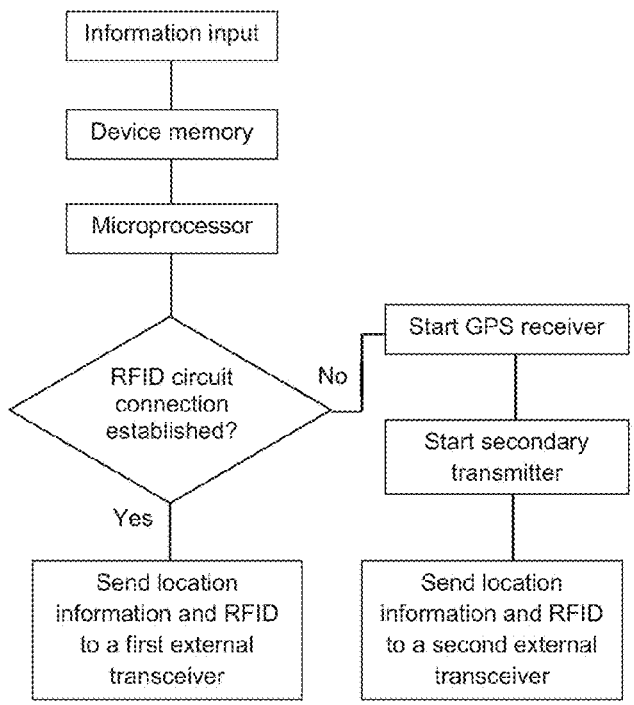
FIG. 6 is an operation block diagram of the tracking device.

Following is a list of elements corresponding to a particular element referred to herein:
  10 tracking system
  100 tracking device
  110 base ring
  112 first half ring
  114 second half ring
  115 outside circumference surface
  116 inner circumference surface
  118 hinge
  120 lock means
  122 key hole
  140 USB port
  150 microprocessor
  155 memory component
  160 radio frequency identification (RFID) circuit
  162 antenna
  170 Global Positioning System (GPS) receiver
  180 power source
  190 alarm component
  260 secondary transmitter
  270 Cardio Respiratory sensor
  310 first external transceiver
  320 second external transceiver
  330 server
  340 view terminal Referring now to FIGS. 1-8, the present invention features a tracking system (10) including a tracking device (100), a first external transceiver (310) and a second external transceiver (320) for tracking a patient and providing patient data.

In some embodiments, the device (100) of the present invention is used as a triage tool, a tracking tool for pediatric patients, a tracking tool for Alzheimer patients, or a means of providing and accessing medical records for managing patient information and patient care. The device (100) can even be used outside a medical facility, such as in a home. The device (100) may be particularly useful for physicians because the physicians can not only locate a patient (e.g., if the patient has moved to a different room suddenly) but access the patient's medical information as well.

The tracking device (100) comprises a base ring (110) divided into a first half ring (112) and a second half ring (114). The ring has an outside circumference surface (115) and an inner circumference surface (116). The base ring (110) is for securing around an individual's wrist or ankle (e.g., an adult, an infant, etc.). The first half ring and second half ring are pivotally connected via a hinge (118). The device (100) (e.g., the first half ring and second half ring) can pivot between an open position (see FIG. 4) and a closed position (see FIG. 1, FIG. 2, FIG. 3). Generally, the base ring (100) is small and compact.

The base ring (110) of the device (100) may be constructed in a variety of materials. For example, in some embodiments, the base ring (110) is constructed from a material making it hard to break, for example a para-aramid synthetic fiber (e.g., Kevlar®). The base ring (110) may comprise a reinforced casing (e.g., an outer shell), which may be constructed from a para-aramid synthetic fiber. For example, the base ring (110) may be constructed from a metal skeleton (e.g., aluminum, lightweight aluminum) and be coated with an outer shell of para-aramid synthetic fiber. The housing may be generally lightweight. In some embodiments, the edges of the base ring (110) are rounded for comfort. Edges of the device (100) may be reinforced for security.

Without wishing to limit the present invention to any theory or mechanism, it is believed that the base ring (110) is advantageous because it is extremely durable (e.g., constructed from para-aramid synthetic fibers), form fitting, and can be used in a variety of ways, for example as an ankle bracelet or a wrist bracelet.

The device (100) can be secured in the closed position via a locking means (120). The locking means (120) is difficult to break. In some embodiments, the locking means (120) includes an optical lock. In some embodiments, the locking means (120) can be unlocked via a key mechanism, for example a keyhole 122 is disposed in the base ring (110). The present invention is not limited to a key mechanism, for example the locking means (120) may include a combination lock, a magnetic lock, a constriction mechanism, the like, or a combination thereof.

The locking means (120) (e.g., optical lock) is operatively connected to an alarm component (190), which is disposed in the base ring. The locking means (120) (e.g., optical lock) is configured to detect tampering (e.g., breakage). When the locking means (120) optical lock) detects tampering the locking means (120) (e.g., optical lock) sends a first alarm input signal to the alarm component to activate the alarm component (190). This alerts others that the user is attempting to break free of the device (100). In some embodiments, the locking means (120) (e.g. optical lock) is operatively connected to a microprocessor (150), which is operatively connected to the alarm component (190). The microprocessor (150) is adapted to receive a first alarm input signal from the locking means (120) (e.g., optical lock) when the locking means (120) (e.g., optical lock) detects tampering, whereupon the microprocessor (150) sends a first alarm output command to the alarm component (190) to active the alarm component.

An active radio frequency identification (RFID) circuit (160), a power source (180) (e.g., a rechargeable battery), and the microprocessor (150) are each disposed in the base ring (110). The microprocessor comprises software and a memory component (155) (e.g., flash memory, read-only memory, random access memory, etc.). The memory component (150) is adapted to store information, for example, patient information (e.g., name, date of birth, medical history, etc.). The memory can be erased and replaced with new information as necessary.

The active RFID circuit (160) is operatively connected to the microprocessor (150) and to an antenna (162) disposed in the base ring (110). The antenna is adapted to send signals from the RFID circuit (160) and receive signals for the RFID circuit (160). The active RFID circuit (160) is adapted to autonomously transmit signals.

RFID circuits are well known to one of ordinary skill in the art. For example, RFID circuits are generally used to track and identify cargo. The active RFID circuit (160) is configured to locate an individual and provide information about the individual via a unique identification (RFID). A first external transceiver (310) can communicate with the active RFID circuit (160) wirelessly, in some embodiments, the first external transceiver (310) is an access point of a hospital alert system. In some embodiments, the first external transceiver (310) is operatively connected to a central server (330), which is accessible by a view terminal (340), such as a personal digital assistant (PDA), a computer, a laptop, a smartphone, etc. via an internet connection.

In some embodiments, the memory (155) of the microprocessor (150) is protected to prevent modification or erasing by unauthorized parties. Examples of protection mechanisms include encryption, password protection, and the like.

The RFID circuit (160) of the present invention is adapted to send signals via the antenna to an external communication system within a range (e.g., 0 to 50 feet, 0 to 100 feet, 0 to 200 feet, 0 to 500 feet, 0 to 750 feet, 0 to 1000 feet, 0 to 1500 feet, 0 to 2000 feet, etc.). In some embodiments, the external communication system is a hospital alert system (e.g., at a nurses' station, etc.) In some embodiments, the hospital alert system is adapted to detect failure to receive the signal from the RFID circuit (160), thereby activating the hospital alert system alarm to alert individuals the patient has left the intended range. Thus, when the RFID circuit (160) is removed from the range, the hospital alert system alarm is activated.

The memory component of the microprocessor may store information including but not limited to an individual's name, age, date of birth, medical information, chart information, medical records, family information, physician's name, the like, or a combination thereof.

In some embodiments, the device 100 further comprises a global positioning system (GPS) receiver (170) and a secondary transmitter (260), both of which are operatively connected to the microprocessor (150). The secondary transmitter (260) is operatively connected to a second external transceiver (320) wirelessly. In some embodiments the GPS receiver may be substituted by a receiver.

Wherein when the communication between the RFID circuit (60) and the first external transceiver (310) is lost, the microprocessor (150) sends a start order to the GPS receiver (170) to start GPS signal receiving for positioning a current location of the tracking device, wherein the microprocessor (150) sends an output of the current location of the device to the secondary transmitter (260), whereupon the secondary transmitter (260) sends the current location information and the signature of the RFID to the second external transceiver (320) with a pre-determined frequency. In some embodiments, the pre-determined frequency is every 10 seconds, 20 seconds, 30 seconds, 1 minute, 2 minutes, or 5 minutes.

In some embodiments, the secondary transmitter is a Bluetooth transmitter or a transmitter using mobile phone data link. In some embodiments, the second external transceiver is a Bluetooth transmitter or a cell phone tower. In some embodiments, the second external transceiver (320) is operatively connected to central server (330), which is accessible by a view terminal (340), such as a personal digital assistant (PDA), a computer, a laptop, a smartphone, etc. via an internet connection in some embodiments, both the first and second external transceivers are accessible by a computer, a smartphone or a personal digital assistant (FDA).

In some embodiments, the tracking device (100) further comprises a Cardio Respiratory sensor (270), which is located on the inner circumference surface (116) to contact the user's skin. The Cardio Respiratory sensor is operatively connected to the microprocessor (150), which is adapted to receive a second alarm input signal from the Cardio Respiratory sensor (270) when the Cardio Respiratory sensor detects a reading below a pre-determined threshold, upon which the microprocessor sends a second alarm output command to the alarm component to activate the alarm component (190).

In some embodiments, the Cardiac sensor is a single lead Pulse Oximetry sensor with a single periodic waveform output with readings for a heartbeat rate or a saturated oxygen percentage. For example, the frequency of the periodic waveform is an index of the heartbeat rate and the amplitude of the periodic waveform is an index of the saturated oxygen percentage.

Figure 7:
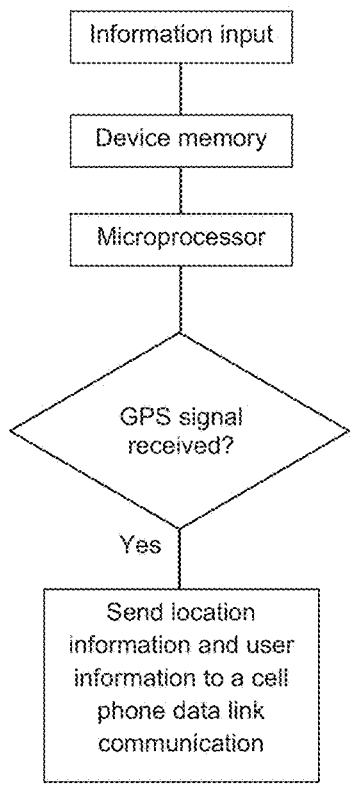
FIG. 7 is an alternative operation block diagram of an alternative tracking device.
Figure 8:
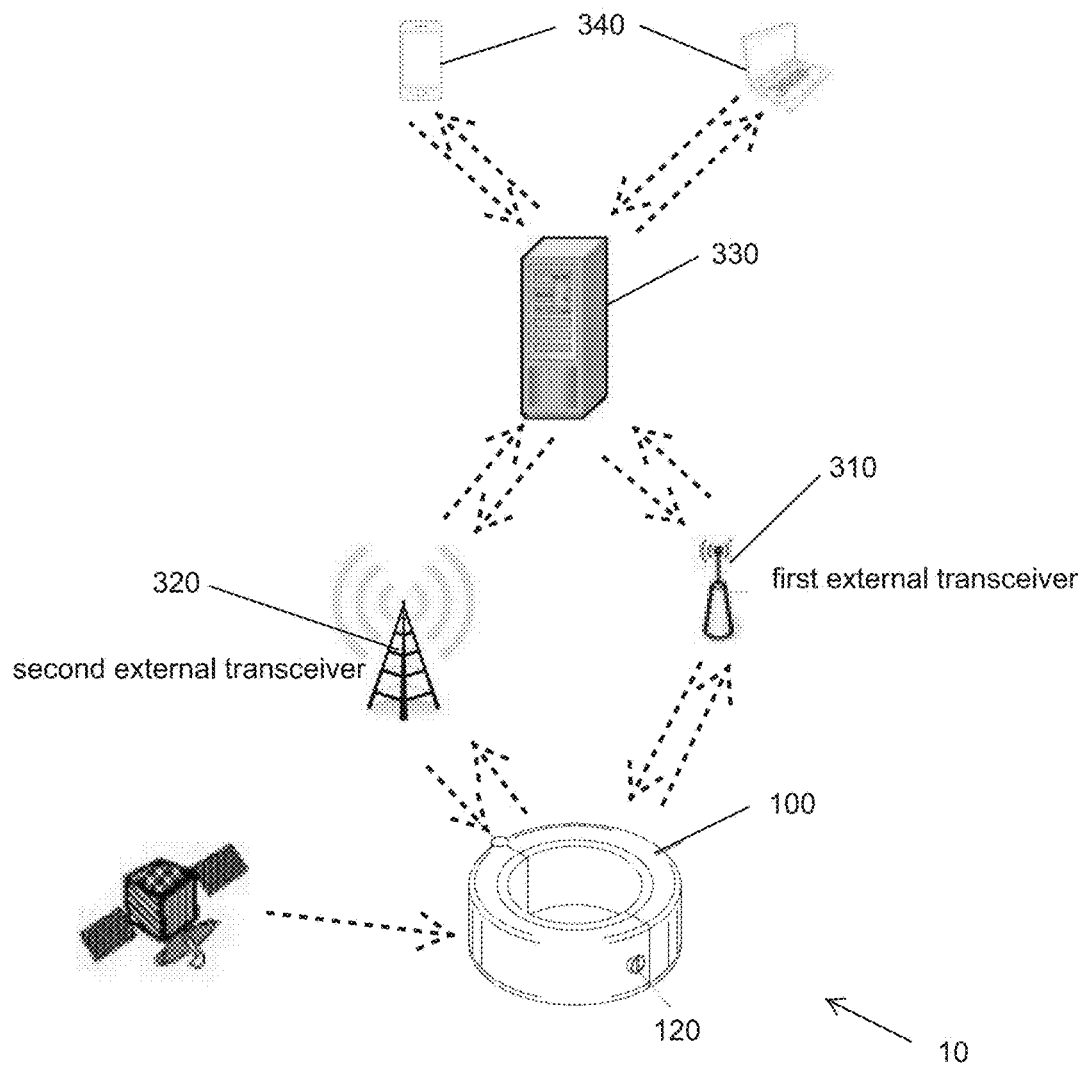
FIG. 8 shows a schematic representation of components of the tracking system of the present invention.

In an alternative embodiment, the tracking system (10) only includes an alternative tracking device (100), and the second external transceiver (320) for tracking a patient and providing patient data. In the alternative embodiment, the alternative tracking device (100) comprises all the components as listed in above except the RFID circuit (160), the antenna (162). In this embodiment, the GPS receiver (170) sends a GPS positioning signal to the microprocessor constantly or on a pre-determined interval. Thereafter, the microprocessor (150) sends an output of the current location of the device to the secondary transmitter (260), upon which the secondary transmitter (260) sends the current location information and a tracking device identification number of the tracking device (100) to the second external transceiver (320) with a pre-determined frequency. An operation block diagram of an alternative tracking device is shown in FIG. 7. In some embodiments, a tracking device identification number is pre-stalled within the memory component (155) during a registration process. In some embodiments, the tracking device is registered from a retail store, from an online website with a computer connected to both the website and the tracking device via USB connection such that the identification number is able to load into the memory component. In some embodiments, an end user needs to pay both the activation fee and the monitoring monthly fee. In some embodiments, the pre-determined frequency is every 10 seconds, 20 seconds, 30 seconds, 1 minute, 2 minutes, or 5 minutes.

The disclosures of the following U.S. Patents are incorporated in their entirety by reference herein. U.S. Provisional Pat. Application Ser. No. 61/077,018; U.S. Pat. No. 6,396,403. U.S. Pat. No. 6,278,370; U.S. Pat. No. 6,169,494; U.S. Pat. Application No. 2004/0080420; U.S. Pat. No. 7,034,690; U.S. Design Pat. No. D547,227.

Various modifications of the invention, in addition to those described herein, will be apparent to those skilled in the art from the foregoing description. Such modifications are also intended to fall within the scope of the appended claims. For example, the above mentioned GPS receiver may be substituted by receiver. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A tracking system (10) comprising:
   (A) a tracking device (100) comprising:
      (a) a base ring (110) formed from a first half ring (112) pivotally attached to a second half ring (114) via a hinge (118), the base ring pivots between at least an open position and a closed position, the base ring is adapted to be secured around a user's wrist or ankle, wherein the ring has an outside circumference surface (115) and an inner circumference surface (116);
      (b) a locking means (120) for securing the base ring in the closed position, the locking means is adapted to detect tampering;
      (c) an alarm component (90) disposed in the base ring;
      (d) a microprocessor (150) comprising software and a memory component (155), the microprocessor is operatively connected to the alarm component, the microprocessor is adapted to receive a first alarm input signal from the locking means (120) when the locking means detects tampering whereupon the microprocessor sends a first alarm output command to the alarm component (190) to activate the alarm component, the memory component (155) is adapted to temporarily store information;
      (e) a universal serial bus (USB) port (140) operatively connected to the microprocessor (150) with the memory components, the USB port allows for data transfer to and from the memory component;
      (f) an active radio frequency identification (RFID) circuit (160) disposed in the base ring, the active RFID has a unique signature, the active RFID circuit is operatively connected to each the microprocessor and to an antenna (162) disposed in the base ring, the antenna is adapted to send signals from the RFID circuit and receive signals for the RFID circuit;
      (g) a Global Positioning System (GPS) receiver (170), wherein the GPS receiver is operatively connected to the microprocessor (150);
      (h) a secondary transmitter (260) operatively connected to the microprocessor;
      (i) a power source (180) operatively connected to at least the active RFID circuit (160), the GPS receiver and the microprocessor;
   (B) a first external transceiver (310), wherein the first external transceiver is configured to communicate with the RFID circuit (160), wherein the active RFID circuit is adapted to autonomously transmit signals within a range to a first external transceiver (310) via the antenna, the signals representing location of the active RFID and information stored on the memory component;
   (C) a second external transceiver (320), wherein the second external transceiver is operatively connected to the secondary transmitter (260) wirelessly;
   wherein when the communication between the RFID circuit (160) and the first external transceiver (310) is lost, the microprocessor (150) sends a start order to the GPS receiver (170) to start GPS signal receiving for positioning a current location of the tracking device, wherein the microprocessor (150) sends an output of the current location of the device to the secondary transmitter (260), whereupon the secondary transmitter (260) sends the current location information and the signature of the RFID to the second external transceiver (320) with a pre-determined frequency.

2. The tracking system of claim 1, wherein the tracking device (100) further comprises a Cardio Respiratory sensor (270), wherein the Cardio Respiratory sensor (270) is located on the inner circumference surface (116) to contact the user's skin, wherein the Cardio Respiratory sensor is operatively connected to the microprocessor (150), wherein the microprocessor is adapted to receive a second alarm input signal from the Cardio Respiratory sensor (270) when the Cardio Respiratory sensor detects a reading below a pre-determined threshold, whereupon the microprocessor sends a second alarm output command to the alarm component to activate the alarm component (190).

3. The tracking system of claim 2, wherein the Cardiac sensor is a single lead Pulse Oximetry sensor with a single periodic waveform output.

4. The tracking system of claim 2, wherein the reading is a heartbeat rate or a saturated oxygen percentage.

5. The tracking system of claim 1, wherein the first external transceiver (310) and the second external transceiver (320) are operatively connected to a central server (330), wherein the central server (330) is accessible by a view terminal (340), wherein the view terminal (340) is a personal digital assistant (PDA), a computer, a laptop, a smartphone.

6. The tracking system of claim 1, wherein the base ring is constructed from a material comprising a para-aramid synthetic fiber.

7. The tracking system of claim 1, wherein the secondary transmitter is a Bluetooth transmitter or a transmitter using mobile phone data link.

8. The tracking system of claim 1, wherein the first external transceiver (310) is an access point of a hospital alert system.

9. The tracking system of claim 1, wherein the second external transceiver is a Bluetooth transmitter or a cell phone tower.

10. The tracking system of claim 1, wherein both the first and second external transceivers are accessible by a computer, a smartphone or a personal digital assistant (PDA).

11. The tracking system of claim 1, wherein the pre-determined frequency is every 10 seconds, 20 seconds, 30 seconds, 1 minute, 2 minutes, or 5 minutes.

12. The tracking system of claim 1, wherein the memory component (155) comprises flash memory, read-only memory, random access memory, or a combination thereof.

13. The tracking system of claim 1, wherein the information stored on the memory component includes a name, an age, a date of birth, a medical history, a physician's name, a medical record, or a combination thereof.

14. The tracking system of claim 1, wherein a keyhole (122) is disposed in the base ring (110) functioning to unlock the locking means (120).

15. A tracking system (10) comprising:
(A) a tracking device (100) comprising:
  (a) a base ring (110) formed from a first half ring (112) pivotally attached to a second half ring (114) via a hinge (115), the base ring pivots between at least an open position and a closed position, the base ring is adapted to be secured around a user's wrist or ankle, wherein the ring has an outside circumference surface (115) and an inner circumference surface (116);
  (b) a locking means (120) for securing the base ring in the closed position, the locking means is adapted to detect tampering;
  (c) an alarm component (190) disposed in the base ring;
  (d) a microprocessor (150) comprising software and a memory component (155), the microprocessor is operatively connected to the alarm component, the microprocessor is adapted to receive a first alarm input signal from the locking means (120) when the locking means detects tampering whereupon the microprocessor sends a first alarm output command to the alarm component (190) to activate the alarm component, the memory component (155) is adapted to temporarily store information including an identification number of the tracking device;
  (e) a universal serial bus (USB) port (140) operatively connected to the microprocessor (150) with the memory components, the USB port allows for data transfer to and from the memory component;
  (f) a Global Positioning System (GPS) receiver (170), wherein the GPS receiver is operatively connected to the microprocessor (150);
  (g) a secondary transmitter (260) operatively connected to the microprocessor;
  (h) a power source (180) operatively connected least the GPS receiver and the microprocessor (150);
(B) a second external transceiver (320), wherein the second external transceiver is operatively connected to the secondary transmitter (260) wirelessly;
wherein the GPS receiver (170) sends a GPS positioning signal to the microprocessor (150) constantly or on a pre-determined interval, whereupon the microprocessor (150) sends an output of the current location of the device to the secondary transmitter (260), whereupon the secondary transmitter (260) sends the current location information and a tracking device identification number of the tracking device (100) to the second external transceiver (320) with a pre-determined frequency.

16. The tracking system of claim 15, wherein the pre-determined frequency is every 10 seconds, 20 seconds, 30 seconds, 1 minute, 2 minutes, or 5 minutes.

17. The tracking system of claim 15, wherein a tracking device identification number is pre-stalled within the memory component (155) during a registration process, wherein the registration process is done at a retail store or at an online website.

18. The tracking system of claim 15, wherein the tracking device (100) further comprises a Cardio Respiratory sensor (270), wherein the Cardio Respiratory sensor (270) is located on the inner circumference surface (116) to contact the user's skin, wherein the Cardio Respiratory sensor is operatively connected to the microprocessor (150), wherein the microprocessor is adapted to receive a second alarm input signal from the Cardio Respiratory sensor (270) when the Cardio Respiratory sensor detects a reading below a pre-determined threshold, whereupon the microprocessor sends a second alarm output command to the alarm component to activate the alarm component (190).

19. The tracking system of claim 15, wherein the Cardiac sensor is a single lead Pulse Oximetry sensor with a single periodic waveform output.

20. The tracking system of claim 15, wherein the second external transceiver (320) is operatively connected to a central server (330), wherein the central server (330) is accessible by a view terminal (340), wherein the view terminal (340) is a personal digital assistant (PDA), a computer, a laptop, a smartphone.

\* \* \* \* \*